United States Patent
Liu et al.

(10) Patent No.: US 9,809,584 B1
(45) Date of Patent: Nov. 7, 2017

(54) SULFUR-CONTAINING OXAZINE COMPOUND AND SYNTHESIS METHOD THEREOF

(71) Applicant: National Tsing Hua University, Hsinchu (TW)

(72) Inventors: Ying-Ling Liu, Hsinchu (TW); Ho-Keng Lin, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 15/359,369

(22) Filed: Nov. 22, 2016

(30) Foreign Application Priority Data

Sep. 10, 2016 (TW) .............................. 105129438 A

(51) Int. Cl.
*C07D 413/14* (2006.01)
*A01N 43/86* (2006.01)

(52) U.S. Cl.
CPC ........... *C07D 413/14* (2013.01); *A01N 43/86* (2013.01)

(58) Field of Classification Search
CPC .............................. C07D 413/14; A01N 43/86
USPC .......................................................... 544/90
See application file for complete search history.

(56) References Cited

U.S. PATENT DOCUMENTS

2014/0309436 A1  10/2014  Greig et al.

FOREIGN PATENT DOCUMENTS

| CN | 1195664 | 10/1998 |
|----|---------|---------|
| CN | 1503788 | 6/2004 |
| CN | 1308310 | 4/2007 |
| TW | I385161 | 2/2013 |
| TW | 201620923 | 6/2016 |

OTHER PUBLICATIONS

Kobayashi et al. Heterocycles (2010), 81(9), 2097-2104.*
Karel Waisser, et al., "A note to the biological activity of benzoxazine derivatives containing the thioxo group," European Journal of Medicinal Chemistry, vol. 45, Issue 7, Jul. 2010, pp. 2719-2725.
Hikmet Agirbas, et al., "Synthesis, IR spectral studies and quantum-chemical calculations on 1,2-dihydronaphto [1,2-e]oxazine-3-thiones and 3,4-dihydrobenzo[e][1,3]oxazine-2-thione," Journal of Molecular Structure, vol. 830, Issues 1-3, Mar. 30, 2007, pp. 116-125.
Karel Waisser et al.,"New groups of antimycobacterial agents: 6-chloro-3-phenyl-4-thioxo-2H-1,3-benzoxazine-2(3H)-ones and 6-chloro-3-phenyl-2H-1,3-benzoxazine-2,4(3H)-dithiones", European Journal of Medicinal Chemistry, vol. 35, Issue 7-8, Aug. 31, 2000, pp. 733-741.
Eva Petrlíková et al.,"Highly active antimycobacterial derivatives of benzoxazine", Bioorganic & Medicinal Chemistry, vol. 18, Issue 23, Dec. 1, 2010, pp. 8178-8187.
"Office Action of Taiwan Counterpart Application," dated May 15, 2017, p. 1-p. 4, in which the listed references were cited.

* cited by examiner

*Primary Examiner* — Kahsay Habte
(74) *Attorney, Agent, or Firm* — J.C. Patents

(57) ABSTRACT

A synthesis method of a sulfur-containing oxazine compound is provided. First, an oxazine compound as a precursor and an elemental sulfur as a feedstock are provided. Then, the elemental sulfur reacts with the oxazine compound directly to form a sulfur-containing oxazine compound.

12 Claims, 2 Drawing Sheets

SULFUR-CONTAINING OXAZINE COMPOUND AND SYNTHESIS METHOD THEREOF

CROSS-REFERENCE TO RELATED APPLICATION

This application claims the priority benefit of Taiwan application serial no. 105129438, filed on Sep. 10, 2016. The entirety of the above-mentioned patent application is hereby incorporated by reference herein and made a part of this specification.

BACKGROUND OF THE INVENTION

Field of the Invention

The invention relates to an oxazine compound and a synthesis method thereof, and more particularly, to a sulfur-containing oxazine compound and a synthesis method thereof.

Description of Related Art

Chemical materials containing sulfur groups have shown wide application potential based on their intriguing properties, including biomedical activity, antibacterial ability, corrosion inhibition, thermal stability and processability. However, the synthesis method of the compound containing a sulfur group requires complicated reaction pathways, and the reaction pathways are difficult to carry out and require reagents that are not easily operative and harmful to the environment. Therefore, the current synthesis of the compound containing a sulfur group is still greatly limited.

SUMMARY OF THE INVENTION

The invention provides a synthesis method of a sulfur-containing oxazine compound having simple, environmentally friendly, and safe steps.

The invention provides a sulfur-containing oxazine compound formed by the synthesis method above.

The synthesis method of the sulfur-containing oxazine compound of the invention includes the following steps. First, an oxazine compound as a precursor and an elemental sulfur as a feedstock are provided. Next, the elemental sulfur is reacted with the oxazine compound directly to form the sulfur-containing oxazine compound.

The sulfur-containing oxazine compound of the invention is formed by the synthesis method of the sulfur-containing oxazine compound.

In an embodiment of the invention, the oxazine compound includes a benzoxazine compound.

In an embodiment of the invention, the oxazine compound includes a difunctional oxazine compound.

In an embodiment of the invention, the oxazine compound includes bis(3-furfuryl-3,4-dihydro-2H-1,3-benzoxazinyeisopropane.

In an embodiment of the invention, the elemental sulfur includes rhombic sulfur ($S_8$).

In an embodiment of the invention, based on 1 equivalent of the α-methylene group of the amine group in the oxazine compound, the amount of the elemental sulfur is 0.1 equivalents or above.

In an embodiment of the invention, based on 1 equivalent of the α-ethylene group of the amine group in the oxazine compound, the amount of the elemental sulfur is 0.5 equivalents or above.

In an embodiment of the invention, based on 1 equivalent of the α-methylene group of the amine group in the oxazine compound, the amount of the elemental sulfur is 1 equivalent or above.

In an embodiment of the invention, the step of reacting the elemental sulfur and the oxazine compound directly includes mixing the elemental sulfur and the oxazine compound using a solvent.

In an embodiment of the invention, the boiling point of the solvent is higher than 115° C.

In an embodiment of the invention, the solvent includes diglyme.

In an embodiment of the invention, the reaction temperature of reacting the elemental sulfur and the oxazine compound directly is 115° C. to 300° C.

In an embodiment of the invention, the sulfur-containing oxazine compound includes bis(3-furfuryl-3,4-dihydro-2H-1,3-benzoxazinyl)isopropane containing a sulfur group.

In an embodiment of the invention, the sulfur-containing oxazine compound has antibacterial activity.

Based on the above, in the invention, an oxazine compound is provided as a precursor and reacted with an elemental sulfur as a feedstock directly to form a sulfur-containing oxazine compound. Therefore, the synthesis method has the advantages of simple steps, low cost, and environmental friendliness. Moreover, the resulting sulfur-containing oxazine compound has antibacterial activity.

In order to make the aforementioned features and advantages of the disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1A:
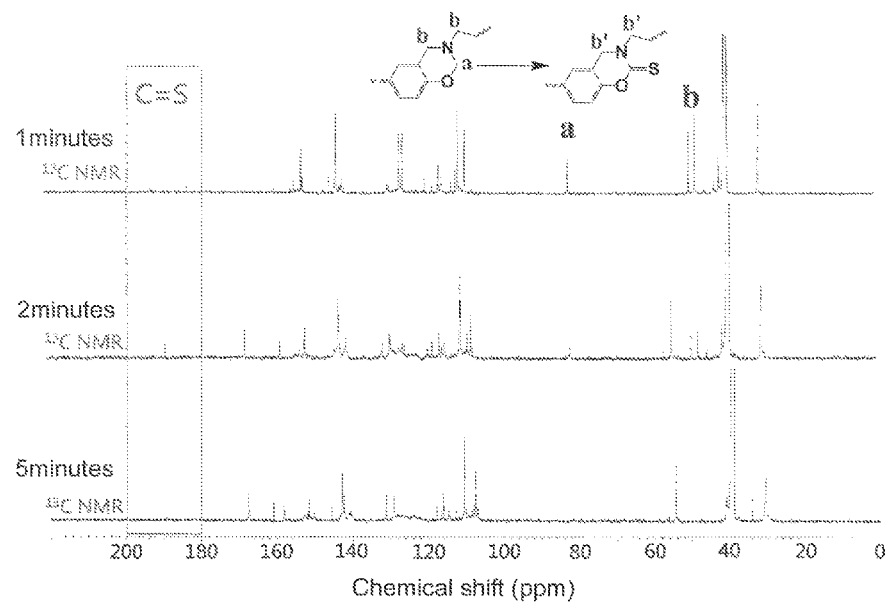
FIG. 1(a) shows the $^{13}$C-NMR for reacting sulfur-containing bis(3-furfuryl-3,4-dihydro-2H-1,3-benzoxazinyl)isopropane samples at 180° C. for 1 minute, 2 minutes, and 5 minutes.

The invention provides a synthesis method of a sulfur-containing oxazine compound, wherein an oxazine compound is provided as a precursor and is reacted with an elemental sulfur as a feedstock directly to form a sulfur-containing oxazine compound.

In the present embodiment, the synthesis method of the sulfur-containing oxazine compound includes, for instance, the following steps. First, the oxazine compound and the elemental sulfur are mixed to form a mixture. In an embodiment, the oxazine compound used as a precursor has the main structure represented by chemical formula 1. In an embodiment, the oxazine compound can be a difunctional oxazine compound prepared with a biosourced furan compound. In the present embodiment, the oxazine compound is, for instance, a benzoxazine compound, and is, for instance, bis(3-furfuryl-3,4-dihydro-2H-1,3-benzoxazinyl) isopropane (BPA-FBz) having chemical formula 2 shown below. The arrows in chemical formula 2 indicates reactive α-methylene (α-CH$_2$) groups of an amino group. In the present embodiment, the oxazine compound has, for instance, advantages such as high thermal stability and high chemical resistance to further chemical reactions. In an embodiment, the elemental sulfur is, for instance, a byproduct of oil refining or sulfur powder from a sulfur-rich ground. In the present embodiment, the elemental sulfur is, for instance, rhombic sulfur (S$_8$). In an embodiment, based on 1 equivalent of the α-methylene groups of the amine group in the oxazine compound, the amount of the elemental sulfur is 0.1 equivalents or above. In an embodiment, based on 1 equivalent of the α-methylene groups of the amine group in the oxazine compound, the amount of the elemental sulfur is 0.5 equivalents or above. In an embodiment, based on 1 equivalent of the α-methylene groups of the amine group in the oxazine compound, the amount of the elemental sulfur is 1 equivalent or above. In the present embodiment, the concentration of the elemental sulfur is, for instance, 10 wt %, 20 wt %, 30 wt %, or 60 wt %. In the present embodiment, the oxazine compound and the elemental sulfur are uniformly mixed by, for instance, a solvent. In the present embodiment, the boiling point of the solvent is higher than 115° C. In the present embodiment, the solvent is, for instance, diglyme.

Next, the oxazine compound and the elemental sulfur are reacted for a period of time at a reaction temperature to form a sulfur-containing oxazine compound. In the present embodiment, the reaction temperature is, for instance, 115° C. to 300° C. In an embodiment, the reaction time is, for instance, 20 minutes to 180 minutes. In the present embodiment, the reaction time is, for instance, 60 minutes. In the present embodiment, the reaction mixture is homogenized within 1 minute and changed into a black substance emitting a gas, wherein the emitted gas is hydrogen sulfide (H$_2$S). In the present embodiment, reagents and catalysts do not need to be added in the reaction process.

In the present embodiment, the reaction scheme is, for instance, represented by reaction formula 1, and the detailed process thereof is, for instance, represented by reaction formula 2.

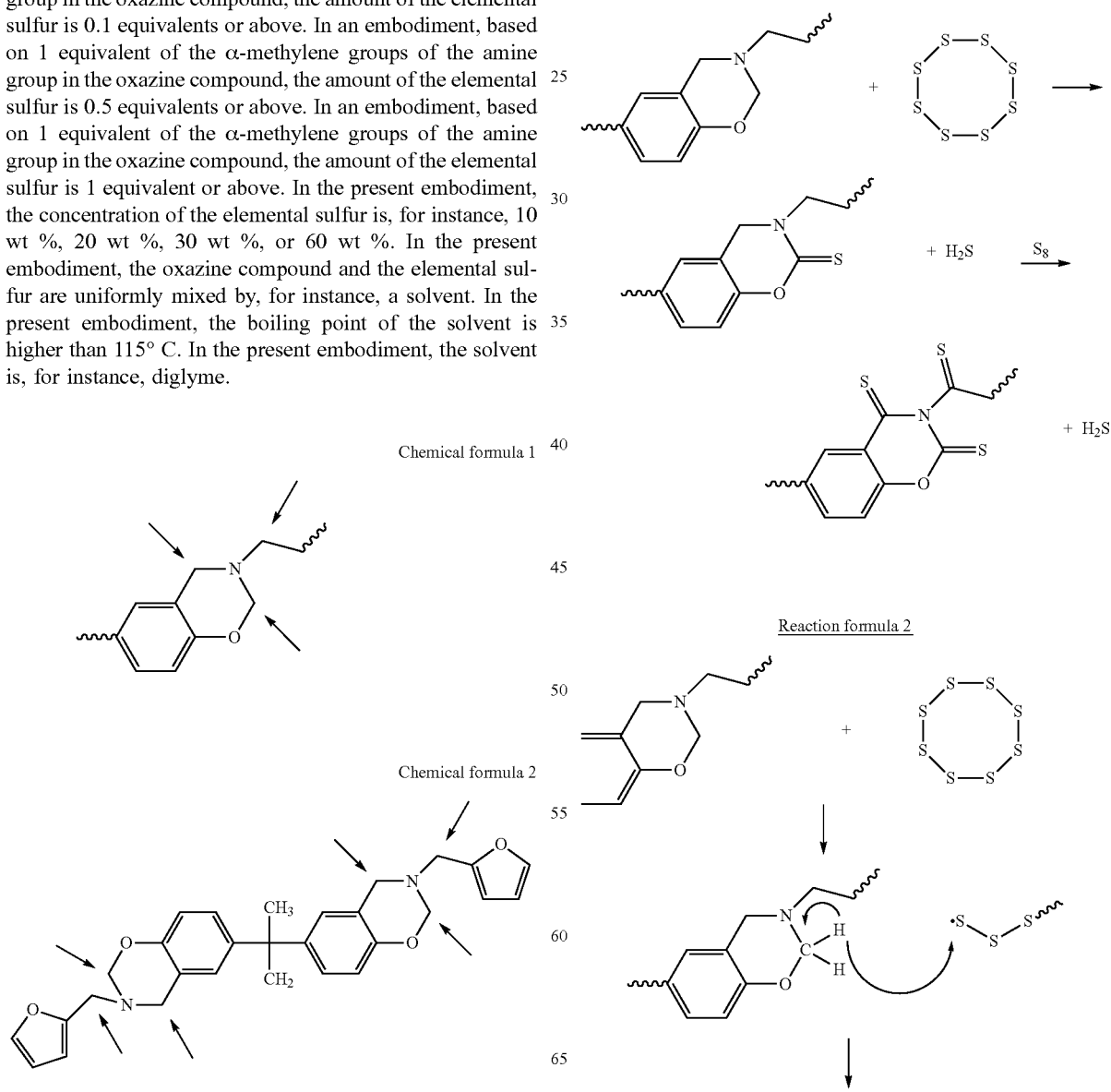

Chemical formula 1

Chemical formula 2

Reaction formula 2

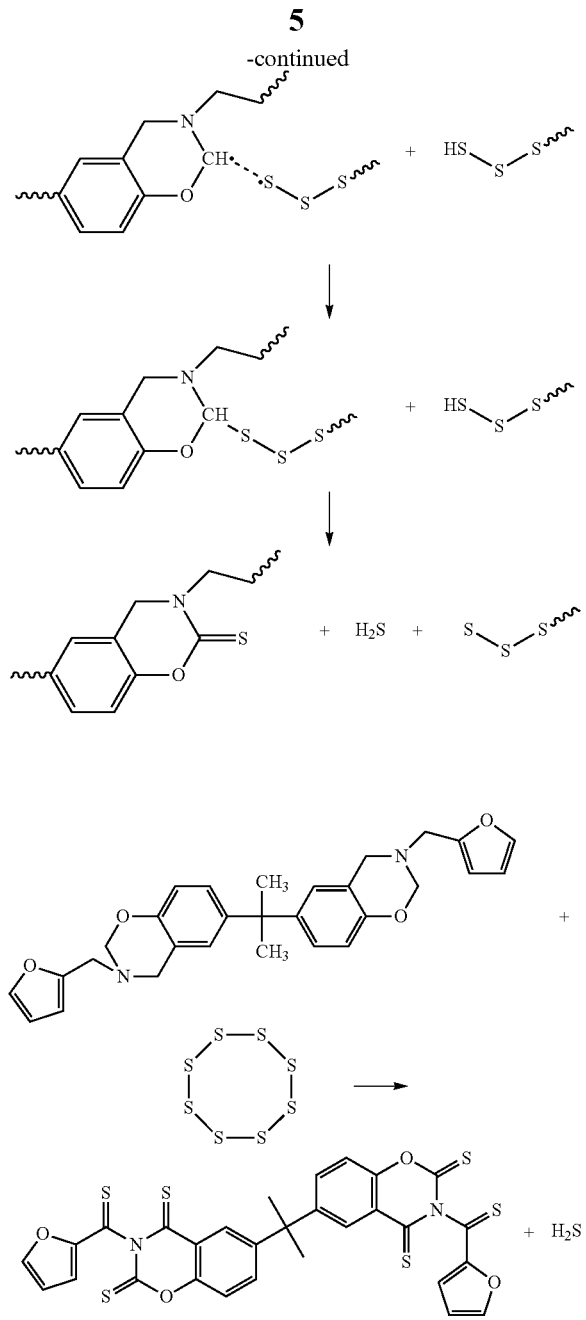

As shown in reaction formula 2, the —CH$_2$— group of the benzoxazine compound has high reactivity in the free radical transfer reaction, and therefore the free radical can be transferred from the elemental sulfur (S$_n$*) to the —CH$_2$— group to produce —HC*— active species and —HS$_n$*—. Next, a free radical coupling reaction occurs to generate —HC(S$_n$)— intermediate. A hydrogen abstraction reaction is performed on —HC(S$_n$)— with HS$_n$* to produce —C(=S)— and H$_2$S as a byproduct. Based on the above reaction scheme, the generation of one sulfur group in the benzoxazine compound requires two sulfur atoms. In other words, the generation of 1 mole of the —C(=S)— group requires 2 moles of sulfur.

In an embodiment, after reacting at 180° C. for 5 minutes, formants (at δ=47 ppm, 49 ppm, and 56 ppm) of α-CH$_2$ tertiary amine is almost not observed in the $^{13}$C-DEPT NMR spectrum. The results further prove that all 3 of the α-CH$_2$ groups (indicated by arrows below) of the tertiary amine in the benzoxazine compound are reactive in the forming of the sulfur group. In the present embodiment, BPA-FBz is used as the benzoxazine compound, and as shown in chemical reaction 2, BPA-FBz has 6 reactive —CH$_2$— groups, and the reaction of reaction formula 3 is carried out, wherein the number of the resulting —C(=S)— group is depended on the sulfur feedstock ratio. Since BPA-FBz has a plurality of reactive sites, the resulting product is indeed a mixture of various sulfur-containing BPA-FBz compounds.

Next, experimental examples are provided to verify the reaction scheme and to measure the properties of the resulting bis(3-furfuryl-3,4-dihydro-2H-1,3-benzoxazinyl)isopropane samples containing a sulfur group.

Figure 1B:
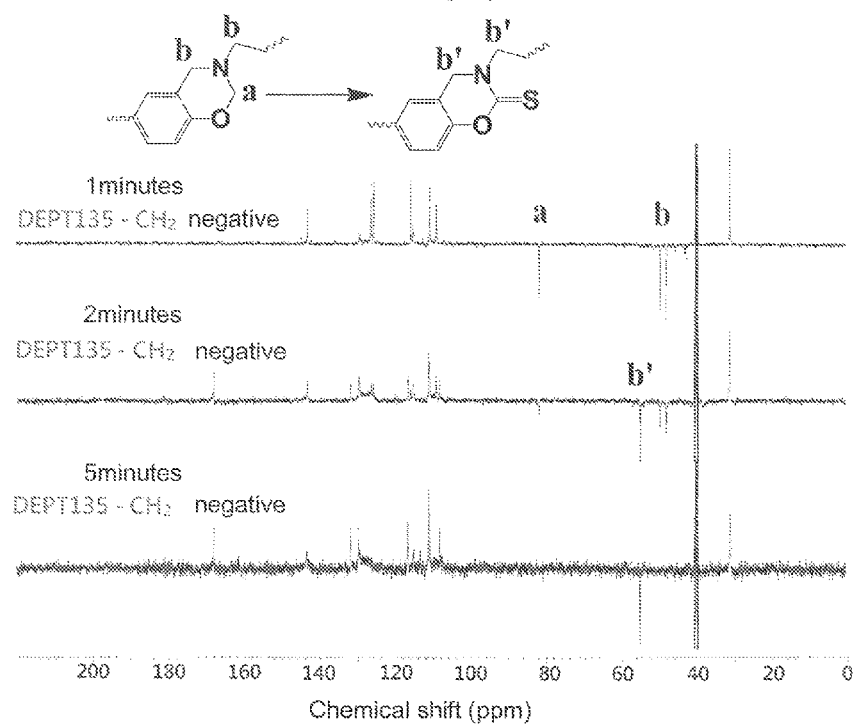
FIG. 1(b) shows the $^{13}$C-DEPT-135 for reacting sulfur-containing bis(3-furfuryl-3,4-dihydro-2H-1,3-benzoxazinyl)isopropane samples at 180° C. for 1 minute, 2 minutes, and 5 minutes.

In an experimental example, a reactant is sampled at different reaction times (respectively a reaction time of 1 minute, 2 minutes, or 5 minutes) and $^{13}$C-DEPT NMR analysis is used to confirm the reactant. The results are shown in FIG. 1. FIG. 1(a) shows the $^{13}$C-NMR for reacting sulfur-containing bis(3-furfuryl-3,4-dihydro-2H-1,3-benzoxazinyl)isopropane samples containing a sulfur group at 180° C. for 1 minute, 2 minutes, and 5 minutes. FIG. 1(b) shows the $^{13}$C-DEPT-135 for reacting sulfur-containing bis (3-furfuryl-3,4-dihydro-2H-1,3-benzoxazinyl)isopropane samples containing a sulfur group at 180° C. for 1 minute, 2 minutes, and 5 minutes. $^{13}$C-DEPT-135 gives all CH$_2$ in a phase opposite to CH and CH$_3$. The formation of the C=S group could be traced with the appearance of the peak at δ=190 ppm, and the peak intensity of O—CH$_2$—N at δ=82 ppm gradually decreases. These results indicate that the first sulfur group forming reaction occurs at the O—CH$_2$—N site of benzoxazine ring. Moreover, the forming of the O—C (=S)—N group brings some deshielding effect to two —N—CH$_2$— groups, so as to shifting the corresponding resonance peaks at δ=49 ppm and δ=47 ppm to δ=56 ppm. At a reaction time of 5 minutes, the resonance peaks at δ=49 ppm and δ=47 ppm completely disappeared, indicating that all O—CH$_2$—N sites were converted to O—C(=S)—N or two —N—CH$_2$— groups involved in the reaction with S$_8$. The results above are consistent with reaction formula 2.

Figure 2A:
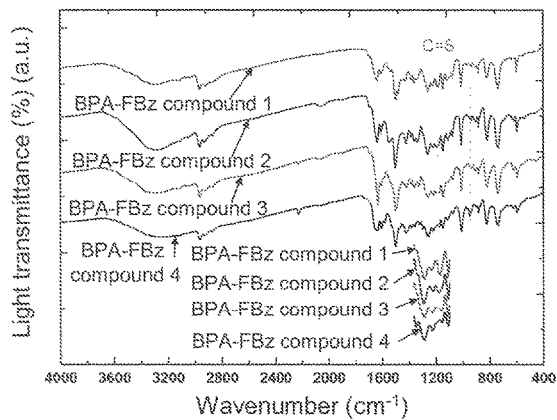
FIG. 2(a) shows the FTIR analysis for sulfur-containing bis(3-furfuryl-3,4-dihydro-2H-1,3-benzoxazinyl)isopropane compounds 1 to 4.
Figure 2B:
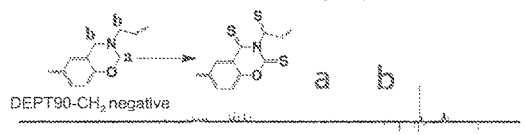
FIG. 2(b) shows a typical $^{13}$C-DEPT spectrum for sulfur-containing bis(3-furfuryl-3,4-dihydro-2H-1,3-benzoxazinyl)isopropane compound 4.
Figure 2B:
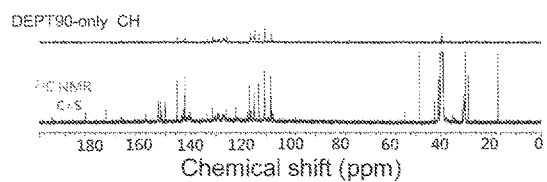
Figure 2C:
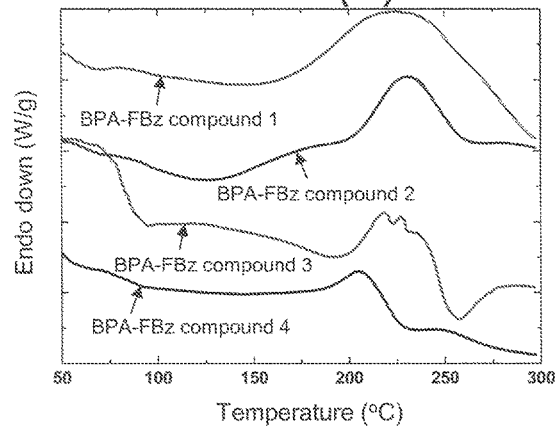
FIG. 2(c) shows the DSC thermogram for sulfur-containing bis(3-furfuryl-3,4-dihydro-2H-1,3-benzoxazinyl)isopropane compounds 1 to 4.

Next, FTIR spectroscopic analysis and DSC thermal analysis are used to confirm the resulting sulfur-containing BPA-FBz compounds, and the results are shown in FIG. 2(a) to FIG. 2(c), wherein sulfur-containing BPA-FBz compounds 1 to 4 are compounds formed by reacting BPA-FBz respectively with 10 wt %, 20 wt %, 30 wt %, and 60 wt % of S$_8$. FIG. 2(a) shows the FTIR analysis for sulfur-containing BPA-FBz compounds 1 to 4. As shown in FIG. 2(a), in the FTIR analysis, the sulfur-containing BPA-FBz compounds show a clear absorbance at 1184 cm$^{-1}$, corresponding to the C=S absorption of the O—C(=S)—N group. Therefore, the O—CH$_2$—N group of the BPA-FBz compounds has relatively high reactivity toward sulfation. Moreover, in the FTIR analysis, since the conjugate length in the compound structure of the sulfur-containing BPA-FBz compounds having higher C=S content is increased, C=S absorption exhibited a red shift. Moreover, the structure of the benzoxazine ring of the sulfur-containing BPA-FBz compounds are characterized with the absorption peaks of N—C—O and C—O—C respectively at 940 cm$^{-1}$ and 1225 cm$^{-1}$.

FIG. 2(b) shows a typical $^{13}$C-DEPT spectrum of sulfur-containing BPA-FBz compound 4. The peak of the sulfur group appears between 180 ppm and 190 ppm. Moreover, the signals of all α-CH$_2$ groups disappear, indicating all possible reactive α-CH$_2$ groups are sulfated into —C(=S)— groups.

FIG. 2(c) shows the DSC thermogram for sulfur-containing BPA-FBz compounds 1 to 4. It can be known from FIG. 2(c) that, sulfur-containing BPA-FBz compounds 1 to 4 respectively exhibits exothermic peak, and the maximum temperature of the exothermic peak decreases with the increasing C=S content in the sulfur-containing BPA-FBz compounds. Similar to the benzoxazine compound, the sulfur-containing BPA-FBz compounds retain thermally crosslinkable properties and can be used as sulfur-containing monomer for preparing of corresponding thermosetting resin with high sulfur content.

Next, sulfur content analysis is used to sulfur-containing BPA-FBz compounds 1 to 4, and the results are shown in Table 1. It can be known from Table 1 that, when the elemental sulfur content in the feedstock is lower (such as 10 wt %), the sulfur content in the resulting sulfur-containing BPA-FBz compounds is in actuality higher than the theoretical value. The reason may be that extra sulfur comes from the side reaction between the resulting $H_2S$ and the benzoxazine compound, and the side reaction may cause an open-ring reaction of a benzoxazine ring. Moreover, the sulfur content in the sulfur-containing BPA-FBz compound formed by 60 wt % of sulfur is in actuality slightly lower than the theoretical value. The reason is that complete conversion of all 6 reactive —$CH_2$— groups in BPA-FBz to C=S is still difficult. However, it can be known from Table 1 that, the method of the present experimental example has a significantly high conversion reaching 80% in the preparation of highly-sulfated BPA-FBz compounds.

TABLE 1

| Sample | Sulfur-containing BPA-FBz compound 1 | Sulfur-containing BPA-FBz compound 2 | Sulfur-containing BPA-FBz compound 3 | Sulfur-containing BPA-FBz compound 4 |
|---|---|---|---|---|
| Sulfur content in feedstock (wt %) | 10 | 20 | 30 | 60 |
| Theoretical sulfur content (wt %) | 5 | 10 | 15 | 29.6 |
| Actual sulfur content (wt %) | 7.6 | 11.4 | 15.1 | 23.7 |

Next, the antibacterial activity of the prepared sulfur-containing BPA-FBz compounds is evaluated using two strains of *staphylococcus* ATTC6341(Sa) and ATTC11632 (Sr), and the results are shown in Table 2. In particular, the Sa strain and the Sr strain have different sensitivities to antibiotics. The Sa strain is penicillin sensitive, and the Sr strain is penicillin resistant, and ampicillin is used as positive control. It can be known from Table 2 that, none of BPA-FBz and sulfur-containing BPA-FBz compounds having low sulfur content (i.e., compounds 1 and 2) has antibacterial activity. However, the sulfur-containing BPA-FBz compounds having high sulfur content (i.e., compounds 3 and 4) both exhibit antibacterial activity in the two strains. Moreover, since the antibacterial activity of the sulfur-containing BPA-FBz compounds having high sulfur content toward the Sr strain is comparable to ampicillin, the sulfur-containing BPA-FBz compounds having high sulfur content have more significant antibacterial activity toward the Sr strain. It can be known from the results that, the introduction of the C=S group in the oxazine compound can significantly increase the antibacterial activity thereof, and therefore the oxazine compound can be extensively applied in biomedical science in the future.

TABLE 2

| | Zone of inhibition (mm) | | | | | |
|---|---|---|---|---|---|---|
| Strain | BPA-FBz | Sulfur-containing BPA-FBz compound 1 | Sulfur-containing BPA-FBz compound 2 | Sulfur-containing BPA-FBz compound 3 | Sulfur-containing BPA-FBz compound 4 | Ampicillin |
| Sa | — | — | — | 11.5 | 11.7 | 34.0 |
| Sr | — | — | — | 9.7 | 10.3 | 9.0 |

Based on the above, the invention provides a chemical method of introducing a sulfur group into an oxazine compound by using an elemental sulfur as a feedstock. The reaction can be applied in other compounds having tertiary amine. Moreover, the sulfated oxazine compound formed by the method exhibits antibacterial activity to a certain degree, and is particularly effective against a penicillin resistant strain. Moreover, since low-costing and abundant elemental sulfur is directly used as a feedstock and a reactant, production cost of the sulfur-containing oxazine compound can be significantly reduced. Moreover, the synthesis method of the invention has the advantages of simplicity and environmental friendliness.

Although the invention has been described with reference to the above embodiments, it will be apparent to one of ordinary skill in the art that modifications to the described embodiments may be made without departing from the spirit of the invention. Accordingly, the scope of the invention is defined by the attached claims not by the above detailed descriptions.

What is claimed is:

1. A synthesis method of a sulfur-containing benzoxazine compound, comprising:
   providing a benzoxazine compound as a precursor and an elemental sulfur as a feedstock, wherein the benzoxazine compound comprises at least one reactive α-methylene (α-$CH_2$) group connecting to an amino group of the benzoxazine; and
   reacting the elemental sulfur and the benzoxazine compound directly to form the sulfur-containing benzoxazine compound, wherein a reaction temperature of reacting the elemental sulfur and the benzoxazine compound directly is 115° C. to 300° C.

2. The synthesis method of claim 1, wherein the-benzoxazine compound comprises a polyfunctional benzoxazine compound.

3. The synthesis method of claim 1, wherein the-benzoxazine compound comprises bis(3-furfuryl-3,4-dihydro-2H-1,3-benzoxazinyl)isopropane.

4. The synthesis method of claim 1, wherein the elemental sulfur comprises rhombic sulfur ($S_8$).

5. The synthesis method of claim 1, wherein based on 1 equivalent of an α-methylene group of an amine group in the benzoxazine compound, an amount of the elemental sulfur is 0.1 equivalents or above.

6. The synthesis method of claim 1, wherein based on 1 equivalent of an α-methylene group of an amine group in the benzoxazine compound, an amount of the elemental sulfur is 0.5 equivalents or above.

7. The synthesis method of claim 1, wherein based on 1 equivalent of an α-methylene group of an amine group in the benzoxazine compound, an amount of the elemental sulfur is 1 equivalent or above.

8. The synthesis method of claim 1, wherein the step of reacting the elemental sulfur and the benzoxazine compound directly comprises mixing the elemental sulfur and the benzoxazine compound using a solvent.

9. The synthesis method of claim 8, wherein a boiling point of the solvent is higher than 115° C.

10. The synthesis method of claim 8, wherein the solvent comprises diglyme.

11. The synthesis method of claim 1, wherein the sulfur-containing benzoxazine compound comprises bis(3-furfuryl-3,4-dihydro-2H-1,3-benzoxazinyl)isopropane containing a sulfur group.

12. The synthesis method of claim 1, wherein the benzoxazine compound is a polymer possessing benzoxazine groups.

\* \* \* \* \*